(12) United States Patent
Niu et al.

(10) Patent No.: US 7,678,776 B2
(45) Date of Patent: Mar. 16, 2010

(54) INCLUSION COMPLEXES OF BUTYLPHTHALIDE WITH CYCLODEXTRIN OR ITS DERIVATIVES, A PROCESS FOR THEIR PREPARATION AND THE USE THEREOF

(75) Inventors: Zhan-qi Niu, Hebei (CN); Kai Zhao, Hebei (CN); Wen-juan Liu, Hebei (CN); Gui-rong Zhou, Hebei (CN); Chao Liu, Hebei (CN); Rong-duan Wang, Hebei (CN); Hong-zhong Yuan, Hebei (CN); Wen-min Guo, Hebei (CN); Sui-chao Yan, Hebei (CN); Min Bai, Hebei (CN)

(73) Assignee: Shijiazhuang Pharma. Group Zhongqi Pharmaceutical Technology (Shijiazhuang) Co., Ltd. (CN)

( * ) Notice: Subject to any disclaimer, the term of this patent is extended or adjusted under 35 U.S.C. 154(b) by 0 days.

(21) Appl. No.: 12/200,130

(22) Filed: Aug. 28, 2008

(65) Prior Publication Data

US 2008/0318898 A1      Dec. 25, 2008

Related U.S. Application Data

(63) Continuation of application No. 10/524,653, filed as application No. PCT/CN02/00579 on Aug. 21, 2002, now abandoned.

(51) Int. Cl.
*A61K 31/724* (2006.01)
*A61K 31/715* (2006.01)
*C08B 37/16* (2006.01)

(52) U.S. Cl. ............... 514/58; 514/54; 536/103; 536/124

(58) Field of Classification Search ............ 514/58, 514/54; 536/103, 124
See application file for complete search history.

(56) References Cited

U.S. PATENT DOCUMENTS 4,727,064 A     2/1988   Pitha

FOREIGN PATENT DOCUMENTS

| CN | 1100097 A | 3/1995 |
| CN | 1257706 A | 6/2000 |
| CN | 1283621 A | 2/2001 |
| CN | 1086942 C | 7/2002 |
| CN | 1136209 C | 1/2004 |

OTHER PUBLICATIONS

Xu et al. (Yaoxue Xuebao (1999), 34(3), 172-175) (Abstract Sent).*
Habon et al. (Pharmazie (1984), 39 (12), pp. 830-834)(Abstract Sent.*
Xu et al. (Yao Xue Xue Bao = Acta Pharmaceuticals Sinica, (May 2001) vol. 36, No. 5, pp. 329-333) (Abstract sent).*
Ilona Habon et al., "Simulation of Pharmacokinetic Behaviour of Drug-Cyclodextrin Complexes," Pharmazie, vol. 39, No. 12, 1984, pp. 830-834.
Thorsteinn Loftsson et al., "2-Hydroxypropyl-β-cyclodextrin: Properties and Usage in Pharmaceutical Formulations," Pharm. Ztg. Wiss., No. 1, 1991, pp. 5-10.
Thorsteinn Loftsson et al., "Pharmaceutical Applications of Cyclodextrins. 1. Drug Solubilization and Stabilization," Journal of Pharmaceutical Sciences, vol. 85, No. 10, Oct. 1996, pp. 1017-1025.
Roger A. Rajewski et al., "Pharmaceutical Applications of Cyclodextrins. 2. In Vivo Drug Delivery," Journal of Pharmaceutical Sciences, vol. 85, No. 11, Nov. 1996, pp. 1142-1169.
Dietmar Bartschat et al., "Stereoisomeric Flavor Compounds. 79. Simultaneous Enantioselective Analysis of 3-Btuylphthalide and 3-Butylhexahydrophthalide Stereoisomers in Celery, Celeriac, and Fennel," J. Agric. Food Chem., vol. 45, No. 12, 1997, pp. 4554-4557.
Xu Haoliang et al., "Effects of 3-n-Butylphthalide on Pial Arteroles in Focal Cerebral Ischemia Rats," Acta Pharmaceutica Sinica, vol. 34, No. 3, Mar. 1999, English Abstract.
Xu Haoliang et al., "Effects of 3-n-butylphthalide on thrombosis formation and platelet function in rats," Acta Pharmaceutica Sinica, vol. 36, No. 5, May 2001, English Abstract.
Thorsteinn Loftsson et al., "Cyclodextrins in drug delivery," Expert Opinion, vol. 2, No. 2, 2005, pp. 335-351.

* cited by examiner

*Primary Examiner*—Shaojia Anna Jiang
*Assistant Examiner*—Michael C Henry
(74) *Attorney, Agent, or Firm*—DLA Piper LLP (US)

(57) ABSTRACT

The present invention relates to the inclusion complexes of butylphthalide, which is D, L-mixed or levorotatory, with cyclodextrin or cyclodextrin derivatives, to a process for their preparation and the use thereof. In the invention, the butylphthalide is complexed with cyclodextrin or cyclodextrin derivatives, preferably with hydroxypropyl-β-cyclodextrin in order to increase the water-solubility of butylphthalide, develop clinical solid or liquid formulations and improve the therapeutic effect of butylphthalide. The inclusion complex, in which the molar ratio of butylphthalide to cyclodextrin or cyclodextrin derivatives is in the range of 1:1-10, can be used to prepare infusion, injection, injectable powder, liquids for oral administration, syrup, tablets, granules, dispersible tablets and others.

4 Claims, No Drawings

INCLUSION COMPLEXES OF BUTYLPHTHALIDE WITH CYCLODEXTRIN OR ITS DERIVATIVES, A PROCESS FOR THEIR PREPARATION AND THE USE THEREOF

TECHNICAL FIELD

The present invention relates to pharmaceutical compositions. More particularly, it relates to the inclusion complexes of butylphthalide, which is D, L-mixed or levorotary, with cyclodextrin or its derivatives, to a process for their preparation and the use thereof.

BACKGROUND ART

Butylphthalide is a water insoluble oily compound with the following formula:

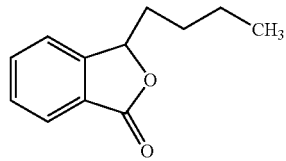

There are two optical isomers, levorotary and dextrorotary butylphthalide, due to the presence of a chiral carbon therein. Chinese patent application No. 98125618.X disclosed the use of levorotary butylphthalide in the preparation of pharmaceutical compositions for preventing thrombosis and platelet agglomeration. It was found that butylphthalide could regulate the function of NOS-NO-cGMP system and the metabolism of arachidonic acid in the neurocytes after ischemia. Chinese patent application No. 93117148.2 disclosed the use of racemic butylphthalide mixture in the preparation of pharmaceuticals for preventing and treating ischemia-induced diseases in mammals or human.

Butylphthalide can be obtained by extraction from natural celery seed oil or by chemical synthesis, as described in Chinese patent application No. 99109673.8 and the prior reference: Junshan Yang, Yalun Su, *Chinese Pharmaceutical Bulletin*, 1984, 31; 671, which realized the availability of butylphthalide.

The pharmaceutical formulations are required to release active agents quickly and exert therapeutic effects rapidly when they are used to treat ischemia-induced diseases or thrombosis. Usually, the formulations for treating acute disease are administrated by intravenous instillation. However, the butylphthalide can only be formulated into soft capsules for oral administration because of its oily characteristics. Therefore, solubility problem of the butylphthalide must be resolved firstly in order to obtain injectable dosage forms.

For the purpose of investigation of the clinical value of butylphthalide, the present applicant has filed a Chinese patent application titled "A inclusion complex of butylphthalide with cyclodextrin derivatives, a process for its preparation and the use thereof" on Jun. 18, 2001, in which solubility problem of butylphthalide was resolved. However, the levorotatory butylphthalide was not mentioned in that application.

DISCLOSURE OF THE INVENTION

The present invention intends to provide inclusion complexes of butylphthalide with cyclodextrin or its derivatives, a process for their preparation and the use thereof. In order to improve water-solubility of butylphthalide, it is complexed with cyclodextrin or its derivatives, wherein the butylphthalide is D, L-mixed or levorotary, and the inclusion complexes may be used to prepare various clinically applicable solid and liquid formulations.

The embodiments according to the present invention are as follows:

An inclusion complex of butylphthalide with cyclodextrin or its derivatives comprises butylphthalide and cyclodextrin oz its derivatives, wherein the molar ratio of butylphthalide to cyclodextrin or its derivatives is in the range of 1:1-10.

The butylphthalide mentioned above comprises D, L-mixed or levorotatory butylphthalide.

The cyclodextrin mentioned above is selected from the group consisting of α-cyclodextrin, β-cyclodextrin, and γ-cyclodextrin.

The derivatives of cyclodextrin mentioned above are selected from the group consisting of hydroxyethyl-β-cyclodextrin, hydroxypropyl-β-cyclodextrin, is dihydroxypropyl-β-cyclodextrin, methyl-β-cyclodextrin, glucose cyclodextrin, maltose cyclodextrin, meltotriose cyclodextrin, carboxymethyl cyclodextrin, and sulfonylalkyl cyclodextrin.

Among the derivatives of cyclodextrin mentioned above, hydroxypropyl-β-cyclodextrin is preferred.

A process for preparing the inclusion complex of butylphthalide with cyclodextrin or its derivatives is provided as follows:

A solution with a concentration of 5-60% is prepared by adding cyclodextrin or its derivatives into a suitable solvent vehicle. A liquid inclusion complex of butylphthalide with cyclodextrin or its derivatives is obtained by adding butylphthalide into the above solution, stirring to provide a clear and transparent solution without oil drops, wherein the molar ratio of butylphthalide to cyclodextrin or its derivatives is in the range of 1:1 to 1:10.

The process mentioned above may further comprise drying the liquid inclusion complex of butylphthalide with cyclodextrin or its derivatives at the temperature of 40-80° C. to obtain a solid inclusion complex of butylphthalide with cyclodextrin or its derivatives.

The process mentioned above may also comprise concentrating the liquid inclusion complex of butylphthalide with cyclodextrin or its derivatives until the concentration of cyclodextrin or its derivatives is 10-15% (W/V), cooling the solution for, e.g. about 12 hours to obtain white precipitate, filtering, and drying at 40-80° C., to obtain a solid inclusion complex of butylphthalide with cyclodextrin or its derivatives.

A process for preparing the inclusion complex of butylphthalide with cyclodextrin or its derivatives according to another aspect of the present invention comprises placing cyclodextrin or its derivatives into a colloid mill or mortar, adding an appropriate amount of suitable solvent vehicle, and stirring the mixture to provide a paste; adding butylphthalide into the paste described above, grinding for about 1-5 hours to provide a homogenous and viscous paste, then filtering the paste, and drying at 40-80° C. to obtain a solid inclusion complex of butylphthalide with cyclodextrin or its derivatives, wherein the molar ratio butylphthalide to cyclodextrin or its derivatives is in the range of 1:1-10.

A process for preparing the inclusion complex of butylphthalide with cyclodextrin or its derivatives according to yet another aspect of the present invention comprises adding cyclodextrin or its derivatives into a suitable solvent vehicle to obtain a solution with a concentration of 5-60%, dissolving the butylphthalide into an appropriate amount of ethanol with purity of 99%, mixing the two solutions, stirring, and drying to obtain a solid inclusion complex of butylphthalide with cyclodextrin or its derivatives, wherein the molar ratio butylphthalide to cyclodextrin or its derivatives is in the range of 1:1-10.

The drying method mentioned above may be any drying method, such as direct drying, spray drying, or freeze-drying.

Examples of the above-mentioned solvent vehicles are water, ethanol, methanol, propanol, isopropanol, ethylene glycol, propylene glycol, glycerin, or acetone, or the mixture of any two or more above-mentioned solvent vehicles, wherein water is preferred.

Such liquid inclusion complex of butylphthalide with cyclodextrin or its derivatives may be directly used to produce liquid formulations, such as infusion, injection, injectable powder, liquids for oral administration, sp, and the like; The solid inclusion complex of butylphthalide with cyclodextrin or its derivatives may be used to produce solid formulations, such as tablets, capsules, granules, dispersible tablets, and the like.

Not wish to be bound by any theory, the inventors believe that cyclodextrin or its derivatives could trap the butylphthalide into their tubular structure to generate an inclusion complex of butylphthalide with cyclodextrin or its derivatives, thereby improving the water-solubility of butylphthalide. Accordingly, the active ingredient butylphthalide in the form of inclusion complexes can be directly applied in solid or liquid dosage forms. Limitations such as poor water-solubility, disability to be directly applied in solid, especially injectable dosage forms can be overcome.

Cyclodextrin or its derivatives are water-soluble pharmaceutical excipients with little toxicity. The inclusion complexes of butylphthalide with cyclodextrin or its derivatives prepared thereby are suitable to be formulated into various liquid and solid dosage forms. The inclusion complexes have the advantages such as good water-solubility and little vascular irritation. The solubility of inclusion complex of butylphthalide with hydroxypropyl-β-cyclodextrin in water at 25° C. is 924 mg/100 ml. The inclusion complex is particularly applicable for preparing liquid dosage forms. The present invention overcomes the limitation that butylphthalide cannot be used to prepare liquid formulations. Due to the fact that the water-solubility is improved, the resulting solid dosage forms have the advantages such as rapid disintegration, good solubility and high bioavailability, which is more applicable for clinical use.

The vascular irritation assay using inclusion complex of butylphthalide with hydroxypropyl-β-cyclodextrin is provided as follows:

Eight rabbits were divided into two groups, namely, test group and control group. For the test group, 2.45 g/kg of the inclusion complex together with 40 ml of 5% glucose were instilled via the marginal ear vein of a rabbit at the rate of 1.5 ml/min. The administration was once per day and lasted for 3 days. For the control group, 10% acetic acid was administrated into the ear vein on one side and 5% glucose injection was instilled into the rabbit ear on the opposite side serving as negative control. The administration lasted for 3 days. Results showed that there was no topical abnormality in the test group after 3 days, similar to the negative control of 5% glucose injection. However, topical hyperaemia, thickening, and exudation were observed after 10% acetic acid injection.

The assay suggests that instillation of the inclusion complex has little vascular irritation, and that the inclusion complex can be used to produce injectable dosage forms.

BEST MODE FOR CARRYING OUT THE INVENTION

In the examples according to the present invention, hydroxypropyl-β-cyclodextrin is preferably used as trapping agent.

In the examples according to the present invention, suitable solvent vehicle for dissolving cyclodextrin or its derivatives is water.

To illustrate the present invention, the following examples are particularly described, but the present invention is not intended to be limited thereto.

Example 1

Preparation of the Solid Inclusion Complex of Butylphthalide with Hydroxypropyl-β-Cyclodextrin The inclusion complex is prepared by (1) weighing 32.38 g (0.0210 mol) hydroxypropyl-β-cyclodextrin, adding it into 400 ml distilled water, and dissolving it with stirring;

(2) weighing 1 g (0.0052 mmol) butylphthalide separately, and adding it into the hydroxypropyl-β-cyclodextrin solution mentioned above;

(3) stirring the mixed solution for 20 minutes by magnetic stirring method at a speed that the solution cannot be spattered, until the solution is clear and transparent, to obtain the liquid inclusion complex of butylphthalide with hydroxypropyl-β-cyclodextrin;

(4) filtering the liquid inclusion complex of butylphthalide with hydroxypropyl-β-cyclodextrin through a film, dividing it into vials, and freeze-drying it.

IR (KBr): 3393.46, 2931.26, 1158.24, 1081.60, 1032.07, 946.55, 580.68. $^{13}$C-NMR: δ 131.47, 105.07, 84.03; 76.29, 75.04, 74.93, 62.89 ppm.

Example 2

Preparation of the Solid Inclusion Complex of Levorotatory Butylphthalide with Hydroxypropyl-β-Cyclodextrin The solid inclusion complex is prepare by (1) weighing 32.38 g (0.0210 mol) hydroxypropyl-β-cyclodextrin adding it into a mixed solvent of 400 ml distilled water and 20 ml absolute ethanol, and dissolving it with stirring;

(2) weighing 1 g (0.0052 mol) levorotatory butylphthalide separately, and adding it into the hydroxypropyl-β-cyclodextrin solution mentioned above;

(3) stirring the mixed solution for 20 minutes by magnetic stirring method at a speed that the solution cannot be spattered, until the solution is clear and transparent, to obtain the liquid inclusion complex of levorotatory butylphthalide with hydroxypropyl-β-cyclodextrin;

(4) concentrating the liquid inclusion complex of levorotatory butylphthalide with hydroxypropyl-β-cyclodextrin, and drying it under reduced pressure, to obtain the solid inclusion complex of levorotatory butylphthalide with hydroxypropyl-β-cyclodextrin.

Example 3

Preparation of the Solid Inclusion Complex of Butylphthalide with Hydroxypropyl-β-Cyclodextrin The solid inclusion complex is prepared by (1) weighing 8.2 g (0.0053 mol) hydroxypropyl-β-cyclodextrin, placing it into a mortar, adding about 4 ml water and grinding the mixture into a paste; then weighing 1 g (0.0052 mol) butylphthalide and adding it into the mortar;

(2) grinding the mixture for 2 hours to obtain a homogenous and viscous paste, filtering the paste, then drying at 60° C. for 4 hours and grinding, to obtain the target inclusion complex.

Example 4

Preparation of Lyophilized Injectable Powder Using the Inclusion Complex of Levorotatory Butylphthalide with Hydroxypropyl-β-Cyclodextrin The lyophilized injectable powder is prepared by (1) weighing 1 g (0.0052 mol) levorotatory butylphthalide;

(2) weighing 82 g (0.053 mol) hydroxypropyl-β-cyclodextrin separately and dissolving it into 150 ml distilled water;

(3) adding the levorotatory butylphthalide into the hydroxypropyl-β-cyclodextrin solution mentioned above and stirring the mixture;

(4) placing the mixture into a freeze drier, freeze-drying and capping to obtain the lyophilized injectable powder.

Example 5

Preparation of Saline Infusion of the Inclusion Complex of Butylphthalide with Hydroxypropyl-β-Cyclodextrin The saline infusion of the inclusion complex is prepared by (1) weighing 32.38 g (0.0210 mol) hydroxypropyl-β-cyclodextrin, adding it into 400 ml distilled water and dissolving with stirring, adding 0.5 g active carbon, then stirring and heating to 80° C. for 14 minutes, and filtering to remove active carbon;

(2) weighing 1 g (0.0052 mol) butylphthalide separately and dissolving it into 10 ml ethanol, adding the solution into the hydroxypropyl-β-cyclodextrin solution mentioned above; and magnetically stirring for 20 minutes (the speed is controlled so that the liquid cannot be spattered) to obtain a clear and transparent solution of the inclusion complex of butylphthalide with hydroxypropyl-β-cyclodextrin without oil drops of butylphthalide;

(3) supplementing water to reach a volume of 800 ml, adding 7-8 g injectable sodium chloride, measuring pH and adjusting the pH to 3.5-7 with 0.05 N of HCl and 0.05 N of NaOH, supplementing water to reach a volume of 1000 ml, adding 0.1 g active carbon, and stirring for 20 minutes;

(4) separating carbon from the solution, filling the solution into bottles (100 ml bottle), and autoclaving at 115° C. for 30 minutes.

Example 6

Preparation of Glucose Infusion of the Inclusion Complex of Butylphthalide with Hydroxypropyl-β-Cyclodextrin The glucose infusion of the inclusion complex is prepared by (1) preparing the solution of the inclusion complex of butylphthalide with hydroxypropyl-β-cyclodextrin as described in step (1) and (2) of EXAMPLE 5;

(2) weighing 50 g injectable glucose, adding water to reach a volume of 100 ml and dissolving with stirring, then adding 0.1 g active carbon and heating the mixture until the mixture begin to boil and maintaining that status for 15 minutes, then removing carbon;

(3) adding the glucose solution into the solution of inclusion complex, supplementing water to reach a volume of 800 ml, and adjusting its pH to 4 with 0.05 N of HCl and 0.05 N of NaOH, supplementing water to reach a volume of 1000 ml, then adding 0.1 g active carbon into the solution, and stirring the solution for 20 minutes;

(4) filtering the solution coarsely and finely with filters or filter stick (pore size of 1.0 μm, 0.45 μm, or 0.22 μm), filling it into bottles and autoclaving at 115° C. for 30 minutes.

Example 7

Preparation of Sterile Injectable Powder Using the Inclusion Complex of Levorotatory Butylphthalide with Hydroxypropyl-β-Cyclodextrin The sterile injectable powder is prepared by (1) weighing 32.38 g (0.0210 mol) hydroxypropyl-β-cyclodextrin in a sterile operation room, dissolving it into water to reach a volume of 90 ml, adding 0.1 g active carbon into the solution, then heating the mixture until the mixture begin to boil and maintaining that status for 15 minutes, and filtering to remove the carbon;

(2) weighing 1 g (0.0052 mol) levorotatory butylphthalide and adding it into the solution of hydroxypropyl-β-cyclodextrin;

(3) magnetically stirring the mixed solution for 20 minutes (the speed is controlled so that the liquid cannot be spattered) to obtain a clear and transparent solution of the inclusion complex of levorotatory butylphthalide with hydroxypropyl-β-cyclodextrin without oil drop of butylphthalide;

(4) supplementing water to reach a volume of 100 ml, filtering through 0.22 μm membrane, filling into 10 ml vials (2-3 ml per vial), freeze drying and capping.

Example 8

Complexation Levorotatory Butylphthalide with β-Cyclodextrin

The complexation process is conducted by

Weighing 3.5 g β-cyclodextrin, adding it into 100 ml distilled water and heating the mixture at 40-60° C. to dissolve β-cyclodextrin, then adding 1 g levorotatory butylphthalide and mechanically stirring for 2-3 hours, cooling in the refrigerator for 4 hours, filtering, washing with ethanol and then drying to obtain the inclusion complex of levorotatory butylphthalide with β-cyclodextrin. The inclusion complex is formulated into various solid dosage forms such as tablets and capsules, etc.

The invention claimed is:

1. A dosage form comprising an inclusion complex of butylphthalide with cyclodextrin derivative which dosage form is an infusion or injection liquid or an injectable powder, wherein said cyclodextrin derivative is selected from the group consisting of hydroxyethyl-β-cyclodextrin, hydroxypropyl-β-cyclodextrin, dihydroxypropyl-β-cyclodextrin, carboxymethyl-cyclodextrin and sulfonylalkyl-cyclodextrin, and the molar ratio of butylphthalide to the cyclodextrin derivative is 1:1 to 1:10.

2. The dosage form according to claim 1, wherein said butylphthalide is D, L-mixed or levorotatory butylphthalide.

3. The dosage form according to claim 1, wherein the cyclodextrin derivative is hydroxypropyl-β-cyclodextrin.

4. The dosage form according to claim 2, wherein the cyclodextrin derivative is hydroxypropyl-β-cyclodextrin.

* * * * *